US012614279B2

(12) United States Patent
Hirano et al.

(10) Patent No.: US 12,614,279 B2
(45) Date of Patent: Apr. 28, 2026

(54) INFORMATION PROCESSING SYSTEM FOR MEDICAL IMAGE DATA, INFORMATION PROCESSING METHOD, INFORMATION TERMINAL, AND NON-TRANSITORY COMPUTER-READABLE MEDIUM

(71) Applicant: CANON KABUSHIKI KAISHA, Tokyo (JP)

(72) Inventors: Yoshinori Hirano, Chiba (JP); Ryuta Ueda, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 907 days.

(21) Appl. No.: 17/815,184

(22) Filed: Jul. 26, 2022

(65) Prior Publication Data

US 2023/0033263 A1 Feb. 2, 2023

(30) Foreign Application Priority Data

Jul. 29, 2021 (JP) ................................. 2021-124635

(51) Int. Cl.
| | |
|---|---|
| *G06N 5/04* | (2023.01) |
| *G06T 7/00* | (2017.01) |
| *G16H 30/40* | (2018.01) |
| *G16H 50/20* | (2018.01) |
| *H04L 67/12* | (2022.01) |

(52) U.S. Cl.
CPC ........... *G06T 7/0014* (2013.01); *G16H 30/40* (2018.01); *G16H 50/20* (2018.01); *H04L 67/12* (2013.01); *G06T 2207/10081* (2013.01); *G06T 2207/10088* (2013.01); *G06T 2207/10132* (2013.01); *G06T 2207/30004* (2013.01)

(58) Field of Classification Search
CPC ........ G06T 7/0014; G06T 2207/20084; G16H 30/20; G16H 30/40; G16H 50/20; G16H 50/70; G06N 20/00; G06N 5/02; G06N 5/04
See application file for complete search history.

(56) References Cited

U.S. PATENT DOCUMENTS

| | | | | |
|---|---|---|---|---|
| 2020/0090810 | A1* | 3/2020 | Sakaguchi | .............. G06N 20/00 |
| 2020/0242762 | A1* | 7/2020 | Matsuki | ................ G06F 18/214 |

FOREIGN PATENT DOCUMENTS

| | | |
|---|---|---|
| JP | 2019074868 A | 5/2019 |
| JP | 2020042810 A | 3/2020 |

* cited by examiner

*Primary Examiner* — Kent Yip
(74) *Attorney, Agent, or Firm* — Canon U.S.A., Inc., IP Division

(57) ABSTRACT

An information processing system includes an information terminal configured to acquire medical image data from a medical image capturing apparatus, a plurality of information processing apparatuses each including an inference unit configured to make an inference about the medical image data by using a learned model, and a selection unit configured to select at least one information processing apparatus from the plurality of information processing apparatuses. The information terminal transmits the medical image data to the information processing apparatus selected by the selection unit, and the information processing apparatus selected by the selection unit makes an inference about the transmitted medical image data and transmits an inference result to the information terminal.

11 Claims, 8 Drawing Sheets

| INFORMATION PROCESSING APPARATUS | REGION | DIAGNOSTIC PURPOSE | MEDICAL IMAGE CAPTURING APPARATUS | LEARNING DATA TYPE | RECOGNITION RATE | NUMBER OF INFERENCE CASES | SATISFACTION |
|---|---|---|---|---|---|---|---|
| 130 | LIVER HEART | HEPATITIS ANGINA MYOCARDIAL INFARCTION | CT MRI | A | 82% | 5000 CASES | ☆☆ |
| 132 | LIVER KIDNEY | LIVER CIRRHOSIS CANCER | CT | B | 72% | 1000 CASES | ☆ |
| 134 | LUNG | OVERALL LUNG DISEASES | CT | B | 88% (LUNG CANCER: 85%) | 3000 CASES | ☆☆ |
| 136 | LUNG | LUNG CANCER | XR CT | C | 95% | 6000 CASES | ☆☆☆ |
| 138 | LUNG LIVER | OVERALL LUNG DISEASES OVERALL LIVER DISEASES | CT MRI | A | 85% (LUNG CANCER: 90%) | 8000 CASES | ☆☆ |

INFERENCE PHASE

INFORMATION PROCESSING SYSTEM FOR MEDICAL IMAGE DATA, INFORMATION PROCESSING METHOD, INFORMATION TERMINAL, AND NON-TRANSITORY COMPUTER-READABLE MEDIUM

BACKGROUND

Field of the Disclosure

The present disclosure relates to an information processing system that makes an inference using a trained model, an information processing method, an information terminal, and a non-transitory computer-readable medium.

Description of the Related Art

A computer aided diagnosis (CAD) system is known that analyzes medical data acquired by a medical image capturing apparatus and presents diagnosis support information to a doctor. The CAD system applies machine learning technology to, for example, medical image data among the medical data and outputs the diagnosis support information.

Japanese Patent Application Laid-Open No. 2020-42810 discusses a technique that acquires a plurality of processed medical signals about an examinee and performs inference by using a plurality of trained models with respect to each of the plurality of processed medical signals, by executing at least one of different image capturing methods and different signal processing in order to improve reliability of analysis based on machine learning. In Japanese Patent Application Laid-Open No. 2020-42810, however, it is not assumed to provide a plurality of information processing apparatuses each including an inference unit that makes an inference about medical image data. Thus, a plurality of information processing apparatuses cannot be used to make an inference.

SUMMARY

The present disclosure is directed to the provision of an information processing system that can select at least one information processing apparatus from a plurality of information processing apparatuses and make an inference.

According to an aspect of the present invention, an information processing system includes an information terminal configured to acquire medical image data from a medical image capturing apparatus, a plurality of information processing apparatuses each including an inference unit configured to make an inference about the medical image data, and a selection unit configured to select at least one information processing apparatus from the plurality of information processing apparatuses. The information terminal transmits the medical image data to the information processing apparatus selected by the selection unit, and the information processing apparatus selected by the selection unit makes an inference about the transmitted medical image data and transmits an inference result to the information terminal.

Further features of the present invention will become apparent from the following description of exemplary embodiments with reference to the attached drawings.

BRIEF DESCRIPTION OF THE DRAWINGS

FIG. 1 illustrates a configuration of an information processing system according to an exemplary embodiment of the present invention.

FIG. 7 illustrates features of a plurality of information processing apparatuses according to an exemplary embodiment of the present invention.

DESCRIPTION OF THE EMBODIMENTS

Figure 2:
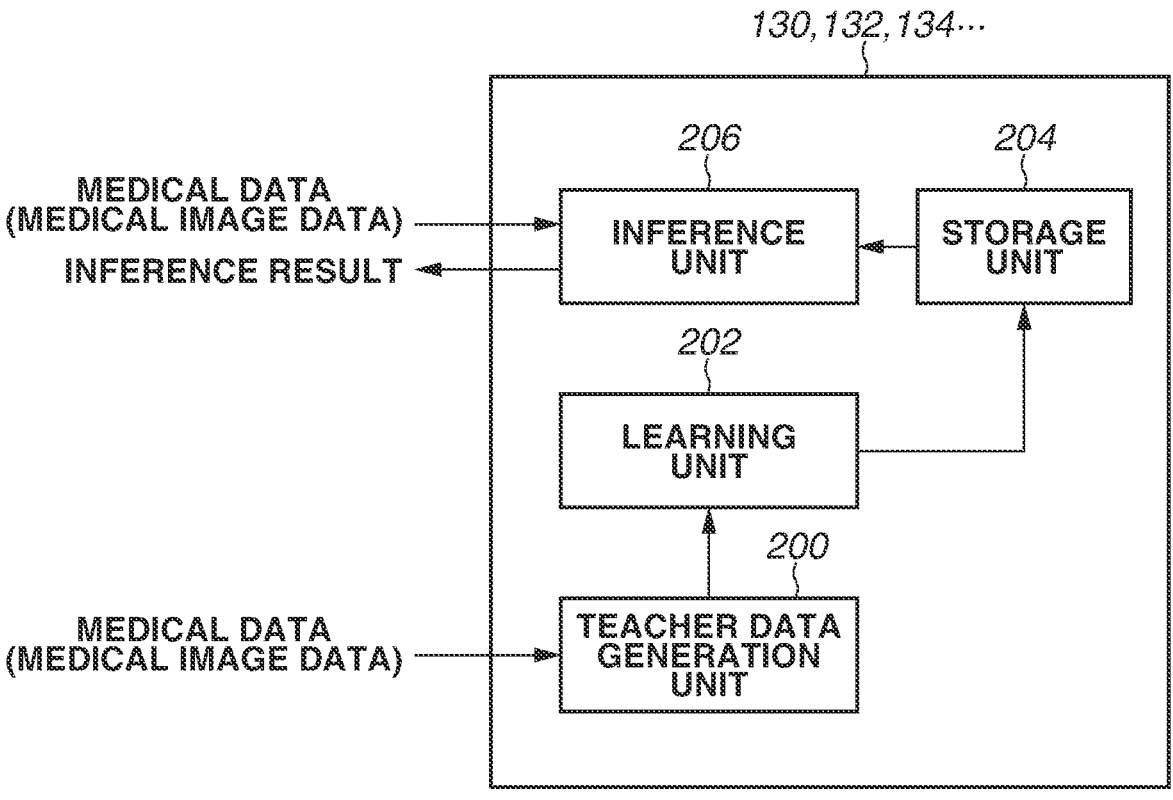
FIG. 2 illustrates a configuration of an information processing apparatus according to an exemplary embodiment of the present invention.

Various exemplary embodiments of the present invention will be described in detail below with reference to the attached drawings.

Figure 1:
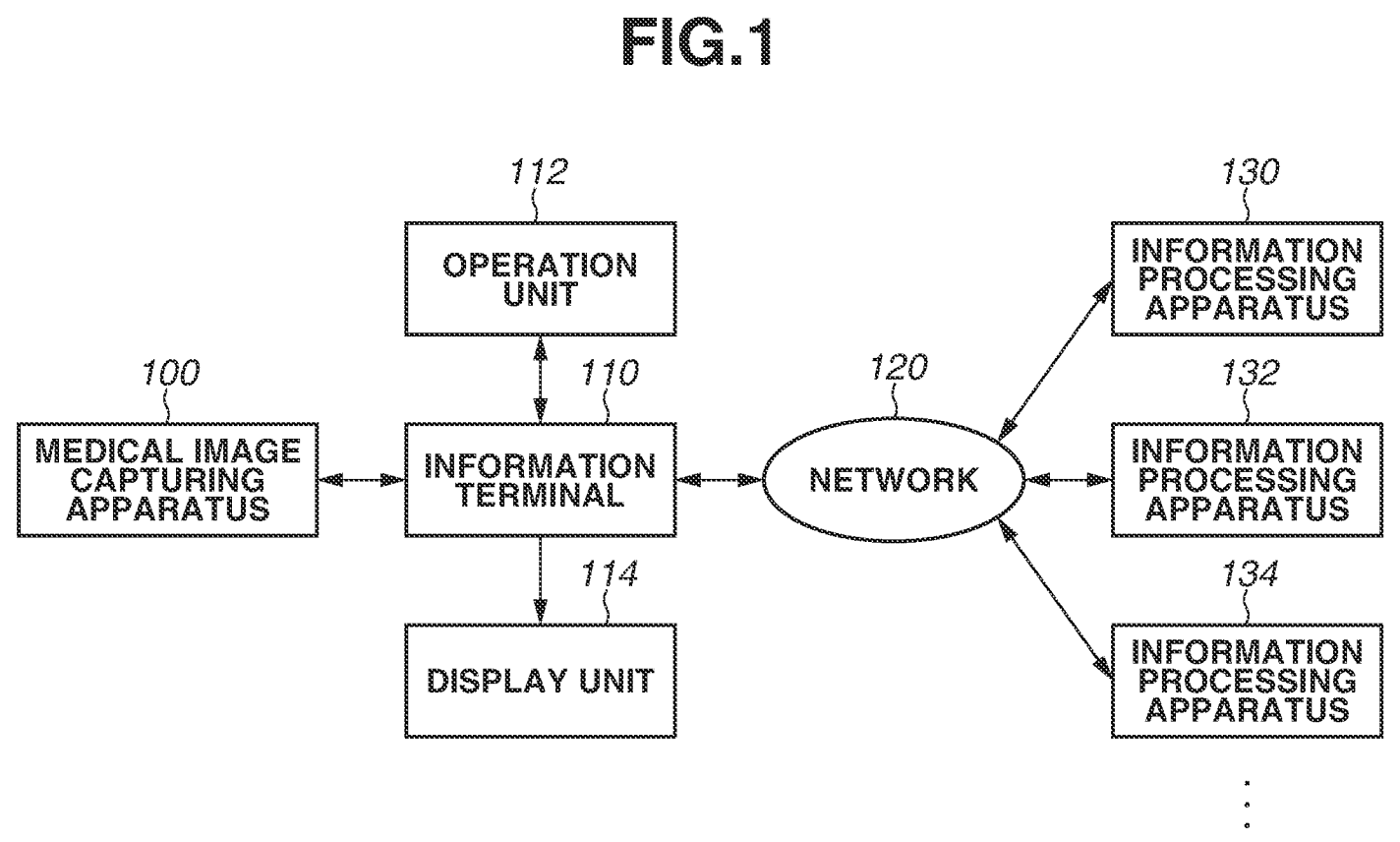

FIG. 1 illustrates a configuration of an information processing system according to a first exemplary embodiment of the present invention. The information processing system according to the present exemplary embodiment includes a medical image capturing apparatus 100 that acquires medical data regarding an examinee, an information terminal 110, a network 120, and a plurality of information processing apparatuses 130, 132, and 134. The plurality of information processing apparatuses may include four or more information processing apparatuses. The information terminal 110 has a function of selecting at least one information processing apparatus from the plurality of information processing apparatuses. The information processing apparatus may be replaced with an information processing function. The information processing system may be provided with a cloud having a plurality of information processing functions. The information processing function is a processing function that can be executed in the cloud.

The information terminal 110 is connected to an operation unit 112 and a display unit 114. The operation unit 112 receives various instructions from an operator and transmits the various instructions to the information terminal 110 and the medical image capturing apparatus 100. The operation unit 112 includes, for example, a mouse, a keyboard, a button, a panel switch, a foot switch, a trackball, and a joystick. The display unit 114 displays a graphical user interface (GUI) for inputting various instructions from the operation unit 112 and medical image data based on medical data acquired by the medical image capturing apparatus 100.

In FIG. 1, the operation unit 112 and the display unit 114 are provided as separate configurations with respect to the information terminal 110, but the information terminal 110 may have functions of the operation unit 112 and the display unit 114 inside.

The medical image capturing apparatus 100 is an apparatus that acquires medical data of an examinee. Examples of the apparatus include an X-ray computed tomography (CT) apparatus, a magnetic resonance imaging (MRI) apparatus, and an ultrasonic diagnostic apparatus.

The X-ray CT apparatus includes an X-ray source and an X-ray detector. The X-ray CT apparatus irradiates an examinee with X-rays from the X-ray source while rotating the X-ray source and the X-ray detector around the examinee and generates CT image data by projecting data detected by the X-ray detector.

The MRI apparatus generates a predetermined magnetic field with respect to an examinee placed in a static magnetic field and generates MRI image data by performing Fourier transform on acquired data.

The ultrasonic diagnostic apparatus transmits an ultrasonic wave to an examinee and receives an ultrasonic wave as a reflected wave from the examinee to generate ultrasonic wave image data.

The medical data (e.g., CT image data, MRI image data, ultrasonic wave image data) generated by the medical image capturing apparatus 100 is three-dimensional data (volume data) or two-dimensional data. The medical data includes, for example, medical image data regarding an examinee. The medical image data also includes raw data. The medical image data may be moving image data including a plurality of pieces of frame data. The medical data also includes measurement data obtained by performing various types of measurement using the medical image data.

The medical image capturing apparatus 100 is connected to the information terminal 110. Examples of the information terminal 110 include a personal computer (PC) terminal, a mobile phone such as a smartphone, a notebook terminal, and a tablet terminal. The information terminal 110 can set examinee information and associate the medical data acquired from the medical image capturing apparatus 100 with the examinee information. The information terminal 110 can also display various data of the medical data and the measurement data acquired from the medical image capturing apparatus 100.

The information terminal 110 and the plurality of information processing apparatuses 130, 132, 134, and others are connected to the network 120. The network 120 includes a communication network outside a hospital, such as wireless communication (Wi-Fi®), the Internet, a wireless base station, a provider, and a communication line. The network 120 may also include an intranet that is a communication network inside the hospital. The information terminal 110 can be connected to and communicate with the plurality of information processing apparatuses 130, 132, 134, and others via the network 120. The information terminal 110 can transmit the medical data (including the medical image data) to the plurality of information processing apparatuses 130, 132, 134, and others. The plurality of information processing apparatuses 130, 132, 134, and others can transmit inference results obtained by making inferences using the medical data (including the medical image data) to the information terminal 110.

The information terminal 110 includes a selection unit that selects at least one information processing apparatus from the plurality of information processing apparatuses 130, 132, 134, and others. Here, it is assumed that the information processing apparatus 130 is selected. The information terminal 110 transmits medical image data to the information processing apparatus 130 selected by the selection unit. The information processing apparatus 130 makes an inference about the transmitted medical image data and transmits an inference result to the information terminal 110.

FIG. 2 illustrates a configuration of the information processing apparatus 130 according to the present exemplary embodiment. The other information processing apparatuses 132, 134, and others include the same configuration as that of the information processing apparatus 130. The information processing apparatus 130 is described here.

The information processing apparatus 130 includes a teacher data generation unit 200, a learning unit 202, a storage unit 204, and an inference unit 206. The teacher data generation unit 200 generates teacher data using the medical image data. The learning unit 202 learns about the medical image data using the teacher data generated by the teacher data generation unit 200. The storage unit 204 stores a trained model generated in the learning unit 202. The inference unit 206 makes an inference using the trained model.

Components (functions) of the information processing apparatus 130 can be realized by, for example, a processor such as a central processing unit (CPU) and a graphics processing unit (GPU) executing a program (software) stored in a memory.

The information processing apparatus 130 includes a processor and a memory inside. The processor can execute each processing of the information processing apparatus 130 based on the program stored in the memory, and can make the information processing apparatus 130 function as, for example, the teacher data generation unit 200, the learning unit 202, the storage unit 204, and the inference unit 206.

The teacher data generation unit 200 is connected to the network 120 and can acquire the medical data including the medical image data and the measurement data. The teacher data generation unit 200 generates teacher data using the medical image data. The teacher data to be generated by the teacher data generation unit 200 is determined depending on a task of an inference to be performed by a neural network and a target of classification.

Examples of the task of the inference to be performed by the neural network include a classification task to classify a medical image data class, a detection task to detect what is captured in which position in the medical image data, and a segmentation task to extract a target area from the medical image data.

In a case where the neural network that performs the classification task is trained, the teacher data generation unit 200 generates teacher data in which the medical image data is paired with a correct label, which is a label indicating a target captured in the medical image data.

In contrast, in a case where the neural network performs the detection task, the teacher data generation unit 200 generates teacher data in which the medical image data is paired with a correct image obtained by adding, to the medical image data, a region of interest (ROI) indicating a position of a target captured in the medical image data and a correct label as a label indicating the target.

In a case where a task to be performed by the neural network is segmentation, the teacher data generation unit 200 generates teacher data in which the medical image data is paired with a correct image obtained by adding, to the medical image data, position information of a pixel of a target captured in the medical image data and a correct label indicating the target.

For example, in a case where the neural network that performs a task to segment presence or absence of a lesion, a type and an area of the lesion from the medical image data acquired from the information terminal 110 is trained, the teacher data generation unit 200 generates teacher data in which the medical image data including a lesion area is paired with a correct image obtained by adding, to the medical image data, information of a correct label indicating the type of the lesion and position information of a pixel of the lesion.

The teacher data generation unit 200 may perform preprocessing of the medical image data depending on the neural network to be trained by the learning unit 202. For example, in a case where a target of an inference by the neural network is the medical image data, the teacher data generation unit 200 performs processing, such as noise removal, filtering, clipping an image, and change of resolution on the acquired medical image data. In a case where a target of an inference is a natural language such as a sentence, the teacher data generation unit 200 performs preprocessing, such as performing morphological analysis and applying a vector conversion technique, on data of a processing target depending on the target of the inference and the task of the neural network.

FIG. 2 illustrates a form in which the teacher data generation unit 200 is included inside the information processing apparatus 130, but the information terminal 110 may include the teacher data generation unit 200 inside. In other words, the teacher data generation unit 200 may be included in the information terminal 110 as a configuration thereof. For example, after the above-described teacher data is generated by the information terminal 110, an inference device may be trained by the learning unit 202 of the information processing apparatus 130 via the network 120.

The learning unit 202 is connected to the teacher data generation unit 200. The learning unit 202 generates a trained model by learning the medical image data in association with the teacher data using the neural network. The trained model represents a parameter determined by executing learning processing up to a predetermined standard and information of a model corresponding to the parameter.

The trained model may be used in training of another model as transfer learning, and learning processing may be further executed on the trained model.

The neural network includes a plurality of layers. Among the neural networks, particularly a convolutional neural network (CNN), which is a kind of deep learning technique, includes a plurality of intermediate layers between an input layer and an output layer, which are not illustrated. The plurality of intermediate layers includes a convolutional layer, a pooling layer, an upsampling layer, and a composition layer. The convolutional layer is a layer in which convolution processing is performed with respect to an input value group. In the convolutional layer, convolution is performed on the input medical image data, and a characteristic of the medical image data is extracted.

The pooling layer is a layer in which processing to reduce the number of output value groups to be less than the number of input value groups is performed by thinning or combining the input value groups. The upsampling layer is a layer in which processing to increase the number of output value groups to be more than the number of input value groups is performed by duplicating the input value group and adding a value interpolated from the input value group. The composition layer is a layer in which value groups, such as an output value group of a certain layer and a pixel value group forming the medical image data, are input from a plurality of sources and combined by being concatenated and added to each other. The number of intermediate layers can be changed at any time based on a learning content.

The storage unit 204 is connected to the learning unit 202. The storage unit 204 stores, for example, the trained model that is trained to extract a type and an area of a lesion in the medical image data. The trained model is generated using, for example, the neural network, but in addition to the CNN and a recurrent neural network (RNN), which are one of the deep learning techniques among the neural network techniques and models derived from the CNN and the RNN, other machine learning techniques may also be used, such as a support vector machine, logistic regression, and random forests and a method based on a rule base.

The inference unit 206 is connected to the network 120 and can acquire the medical data including the medical image data and the measurement data. The inference unit 206 is connected to the storage unit 204 and can make an inference using the trained model stored in the storage unit 204.

The inference unit 206 makes an inference about newly generated medical image data using, for example, the trained model that is trained to extract the type and the area of the lesion in the medical image data. In a case where the newly generated medical image data includes a lesion, the inference unit 206 can output the type and the area of the lesion.

Figure 3:
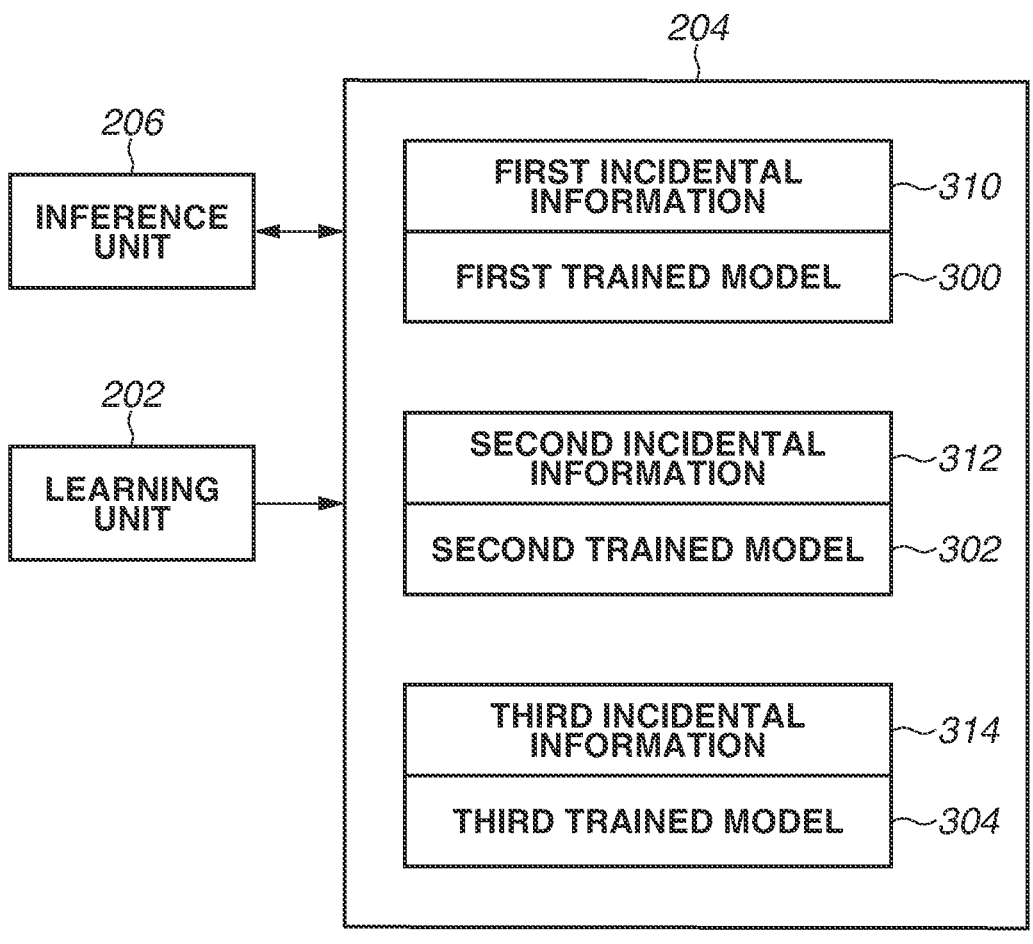
FIG. 3 illustrates a configuration of a storage unit in the information processing apparatus according to an exemplary embodiment of the present invention.

FIG. 3 illustrates a configuration of the storage unit 204 according to the present exemplary embodiment. The storage unit 204 stores the trained model trained by the learning unit 202 and incidental information. Specifically, the storage unit 204 adds first incidental information 310 to a first trained model 300 trained by the learning unit 202 and stores the first trained model 300. The storage unit 204 adds second incidental information 312 to a second trained model 302 trained by the learning unit 202 and stores the second trained model 302. The storage unit 204 adds third incidental information 314 to a third trained model 304 trained by the learning unit 202 and stores the third trained model 304.

FIG. 3 illustrates a form in which three trained models are stored in the storage unit 204 together with the incidental information, but the storage unit 204 can store four or more trained models together with the incidental information. A plurality of the trained models is different from each other in any one of an inferring task, a class indicating a classification target, a model structure, and teacher data. Each trained model can be designated or identified based on the incidental information to be added thereto. The inference unit 206 selects an appropriate trained model based on the incidental information in response to an input from the information terminal 110 and executes inference processing with respect to inference target data acquired from the information terminal 110 using the selected trained model.

The incidental information includes information, such as a region that can be inferred using the trained model, a type of the medical image capturing apparatus (a type of the medical image data), a diagnostic purpose (a diagnostic item), and a type of learning data.

The incidental information is described in detail below.

Figure 4:
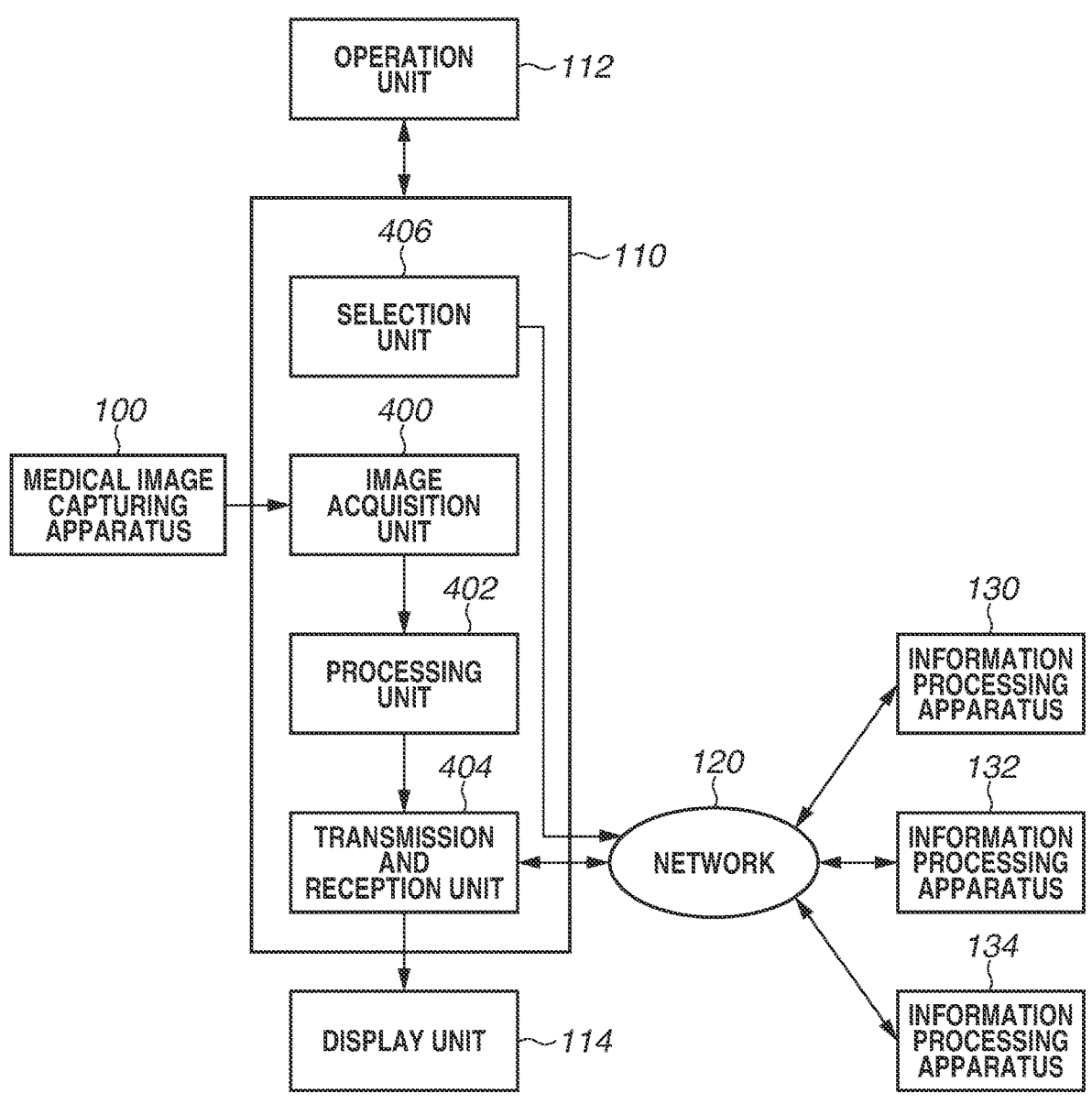
FIG. 4 illustrates a configuration of an information terminal according to an exemplary embodiment of the present invention.

FIG. 4 illustrates a configuration of the information terminal 110 according to the present exemplary embodiment. The information terminal 110 has a function of selecting the information processing apparatus, a function of performing preprocessing of inference processing, a function of transmitting and receiving information, and other functions. FIG. 4 illustrates a form in which the information terminal 110 does not perform the inference processing, and the information processing apparatuses 130, 132, 134, and others perform the inference processing.

The information terminal 110 includes an image acquisition unit 400, a processing unit 402, and a transmission and reception unit 404. The image acquisition unit 400 acquires the medical image data from the medical image capturing apparatus 100. The processing unit 402 performs various processing with respect to the medical image data. The transmission and reception unit 404 transmits the medical image data processed by the processing unit 402 to an external apparatus, such as the information processing apparatus 130, via the network 120. The transmission and reception unit 404 receives information transmitted from the external apparatus, such as the information processing apparatus 130, via the network 120. The display unit 114 displays a medical image based on the medical image data and the information transmitted from the external apparatus, such as the information processing apparatus 130. The processing unit 402 performs, for example, noise removal processing, and gradation conversion processing on the medical image data acquired by the image acquisition unit 400.

The information terminal 110 further includes a selection unit 406 that selects at least one information processing apparatus from the plurality of information processing apparatuses 130, 132, 134, and others. The selection unit 406 transmits the medical image data from the information terminal 110 and selects the information processing apparatus that makes an inference. The transmission and reception unit 404 receives information transmitted from the information processing apparatus selected by the selection unit 406 via the network 120. In other words, the selection unit 406 selects an information processing apparatus that makes an inference about the medical image data. In a case where the plurality of information processing apparatuses 130, 132, 134, and others exists in different clouds and connection formats of the clouds are different, the transmission and reception unit 404 changes the connection format (e.g., a physical connection type, and a logical connection type) of the cloud. Thus, the connection format of the cloud is changed, and the transmission and reception unit 404 is connected to the information processing apparatus selected by the selection unit 406. The physical connection type is, for example, a format in which a router corresponding to the transmission and reception unit 404 is physically connected to a public cloud by a dedicated line. The logical connection type is a format for performing, for example, Packet Data Network (PDN) connection is made with the transmission and reception unit 404.

Figure 5:
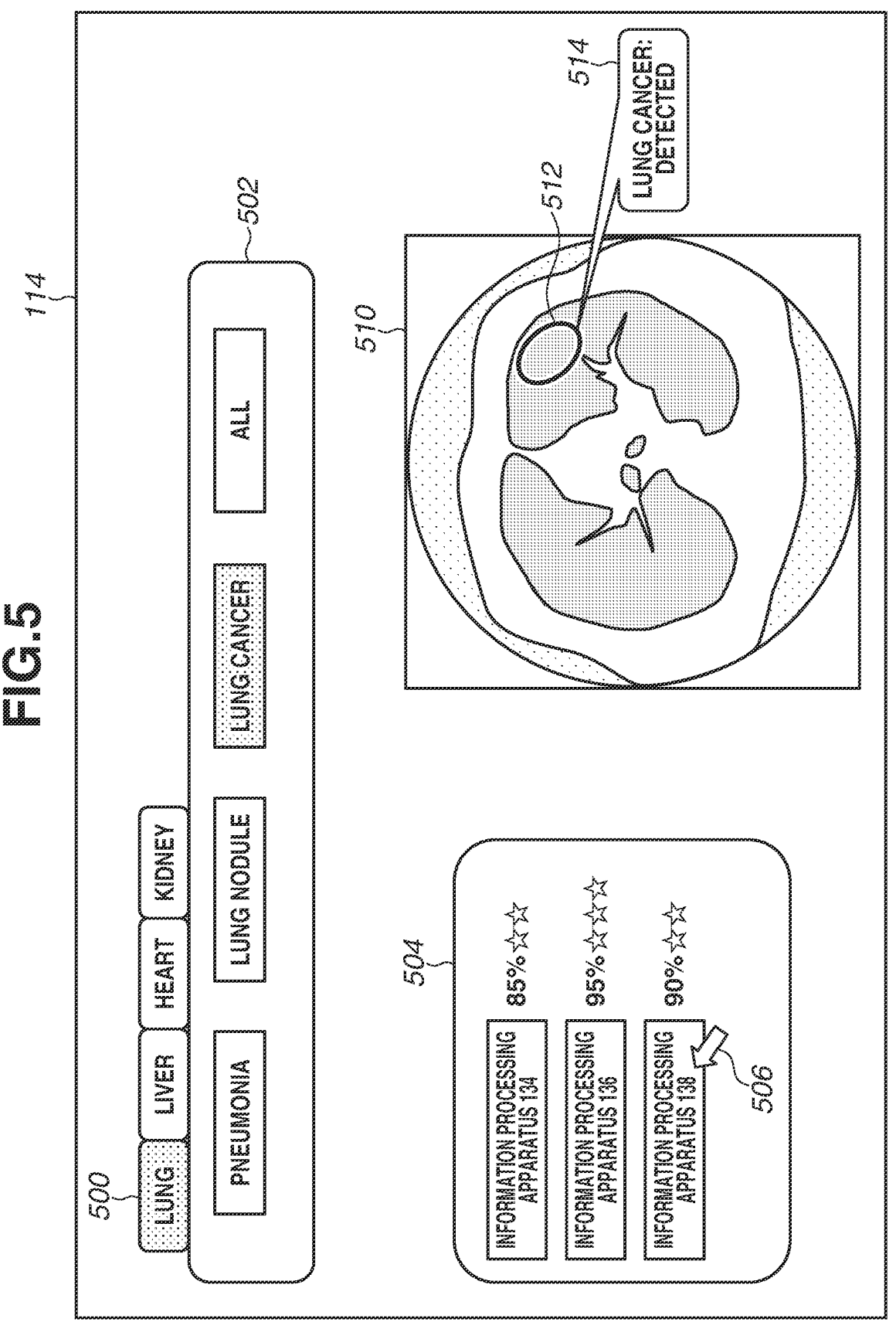
FIG. 5 illustrates one display form of a display unit according to an exemplary embodiment of the present invention.

FIG. 5 illustrates an example of a screen display form of the display unit 114 according to the present exemplary embodiment. The display unit 114 displays a selection screen 504 for selecting the information processing apparatus. An operator can select at least one information processing apparatus from the plurality of information processing apparatuses displayed on the selection screen 504. The selection screen 504 serves as the selection unit 406 for selecting the information processing apparatus.

The display unit 114 displays selection screens 500 and 502 for selecting a diagnosis region and a diagnostic purpose corresponding to the diagnosis region. In FIG. 5, lung, liver, heart, and kidney are displayed as the diagnosis regions. These regions are regions that can be inferred by the plurality of information processing apparatuses 130, 132, 134, and others connected to the network 120. The information terminal 110 acquires, from the plurality of information processing apparatuses, the incidental information corresponding to the regions that can be inferred by the respective information processing apparatuses. In a case where the information terminal 110 executes (requests) an inference about the medical image data, the information terminal 110 inquires of the plurality of information processing apparatuses 130, 132, 134, and others connected to the network 120. The information terminal 110 then acquires the regions that can be inferred by the plurality of information processing apparatuses 130, 132, 134, and others from the plurality of information processing apparatuses 130, 132, 134, and others. The information terminal 110 may store the incidental information corresponding to the regions that can be inferred by the respective information processing apparatuses in advance. The information terminal 110 may also acquire, for example, the incidental information corresponding to a type of the medical image capturing apparatus, the diagnostic purpose (a diagnostic item), the type of learning data, a recognition rate, the number of inference cases, and satisfaction that can be inferred by the respective information processing apparatuses from the plurality of information processing apparatuses 130, 132, 134, and others.

The information terminal 110 acquires the incidental information corresponding to the regions that can be inferred by the respective information processing apparatuses from the plurality of information processing apparatuses, and the display unit 114 displays region information. In other words, the display unit 114 displays the regions that can be inferred by the respective information processing apparatuses based on the incidental information of the respective information processing apparatuses. Thus, the operator can recognize that a lung, a liver, a heart, and a kidney can be inferred, but other regions such as a pancreas or a head cannot be inferred.

On the selection screen 500 displayed by the display unit 114, tags corresponding to the diagnosis regions are displayed. Further, icons corresponding to the diagnostic purposes (diagnostic items) are also displayed on the selection screen 502. The operator can select the diagnosis region by selecting the tag corresponding to the diagnosis region from the selection screen 500. Further, the operator can select the diagnostic purpose by selecting the icon corresponding to the diagnostic purpose from the selection screen 502.

On the selection screen 502 displayed by the display unit 114, the diagnostic purposes are displayed, such as pneumonia, a lung nodule, a lung cancer, and ALL. They are the diagnostic purposes that can be inferred by the plurality of information processing apparatuses 130, 132, 134, and others connected to the network 120.

The information terminal 110 acquires the incidental information corresponding to the diagnostic purposes that can be inferred by the respective information processing apparatuses from the plurality of information processing apparatuses in advance. The information terminal 110 then acquires the incidental information corresponding to the diagnostic purposes (lesion information) that can be inferred by the respective information processing apparatuses from the plurality of information processing apparatuses. The information terminal 110 may also store the incidental information corresponding to the diagnostic purposes (lesion information) that can be inferred by the respective information processing apparatuses. The display unit 114 can display the diagnostic purpose that can be inferred based on the incidental information of the respective information processing apparatuses. Thus, the operator can recognize that pneumonia, a lung nodule, and a lung cancer can be inferred, but the other diagnostic purposes such pneumothorax cannot be inferred.

The operator can extract the information processing apparatus that detects pneumonia, the information processing apparatus that detects a lung nodule, and the information processing apparatus that detects a lung cancer, by selecting the icon corresponding to the diagnostic purpose. The operator can also extract the information processing apparatus that can handle overall lung diseases by selecting an ALL icon.

In FIG. 5, the icon corresponding to a lung cancer is selected. The information terminal 110 can extract the information processing apparatus that can handle a lung cancer by referring to the incidental information (the diagnostic purposes) of the plurality of information processing apparatuses (storage units). On the selection screen 504, the information processing apparatus that can infer a lung cancer is displayed. In FIG. 5, the information processing apparatuses 134, 136, and 138 are displayed. The display unit 114 can display the plurality of information processing apparatuses 134, 136, and 138 corresponding to the diagnostic purpose of a lung cancer. The operator selects at least one information processing apparatus from the plurality of information processing apparatuses 134, 136, and 138. The operator can select the information processing apparatus using a cursor 506.

In a case where the information processing apparatus 138 is selected by the selection unit 406 of the information terminal 110, the information terminal 110 transmits the medical image data to the information processing apparatus 138 selected by the selection unit 406. The information processing apparatus 138 makes an inference about the transmitted medical image data and transmits an inference result to the information terminal 110. At that time, the information processing apparatus 138 makes the inference about the medical image data transmitted from the information terminal 110 using the trained model that is trained to extract a lung cancer in the medical image data. In a case where the medical image data transmitted from the information terminal 110 includes a lesion of a lung cancer, the information processing apparatus 138 transmits a diagnostic name and area information about the lung cancer to the information terminal 110.

The display unit 114 displays a medical image 510 based on the medical image data. The medical image 510 is one of a plurality of slice images of a CT image (three-dimensional volume data). The information processing apparatus 138 makes the inference about the medical image data transmitted from the information terminal 110 using the trained model corresponding to lung cancer. As illustrated in FIG. 5, for example, in a case where the inference unit 206 of the information processing apparatus 138 detects a lung cancer in the CT image, the information processing apparatus 138 transmits a diagnostic name and area information about the lung cancer to the information terminal 110. The display unit 114 displays detection information 514 indicating that the lung cancer is detected. The display unit 114 also displays an area 512 in which the lung cancer is detected.

On the selection screen 504, the plurality of information processing apparatuses 134, 136, and 138 that can infer the lung cancer are displayed. The selection unit 406 of the information terminal 110 may select at least one information processing apparatus based on the incidental information of the plurality of information processing apparatuses 134, 136, and 138. Specifically, the selection unit 406 of the information terminal 110 can automatically select the information processing apparatus from information (a parameter) based on the incidental information of the plurality of information processing apparatuses 134, 136, and 138. For example, the selection unit 406 compares the recognition rate in the incidental information of the plurality of information processing apparatuses 134, 136, and 138 with each other to select the information processing apparatus 136, which has the highest recognition rate. The selection unit 406 compares the number of inference cases in the incidental information of the plurality of information processing apparatuses 134, 136, and 138 with each other to select the information processing apparatus 136, which has the largest number of inference cases. Information based on the incidental information (for example, a recognition rate or a number of inference cases) can be arbitrarily selected by the operator.

The inference can also be made using the plurality of information processing apparatuses. The operator selects the plurality of information processing apparatuses 136 and 138 from the plurality of information processing apparatuses

134, 136, and 138 using the cursor 506. The information terminal 110 transmits the medical image data to the plurality of information processing apparatuses 136 and 138 that has been selected by the selection unit 406. The plurality of information processing apparatuses 136 and 138 selected by the selection unit 406 respectively make inferences about the transmitted medical image data using the trained model. The plurality of information processing apparatuses 136 and 138 respectively transmit a plurality of inference results obtained by making the inferences about the medical image data to the information terminal 110. The information terminal 110 integrates the plurality of inference results transmitted from the plurality of information processing apparatuses 136 and 138. The display unit 114 displays the integrated inference result together with the medical image data.

Figure 6:
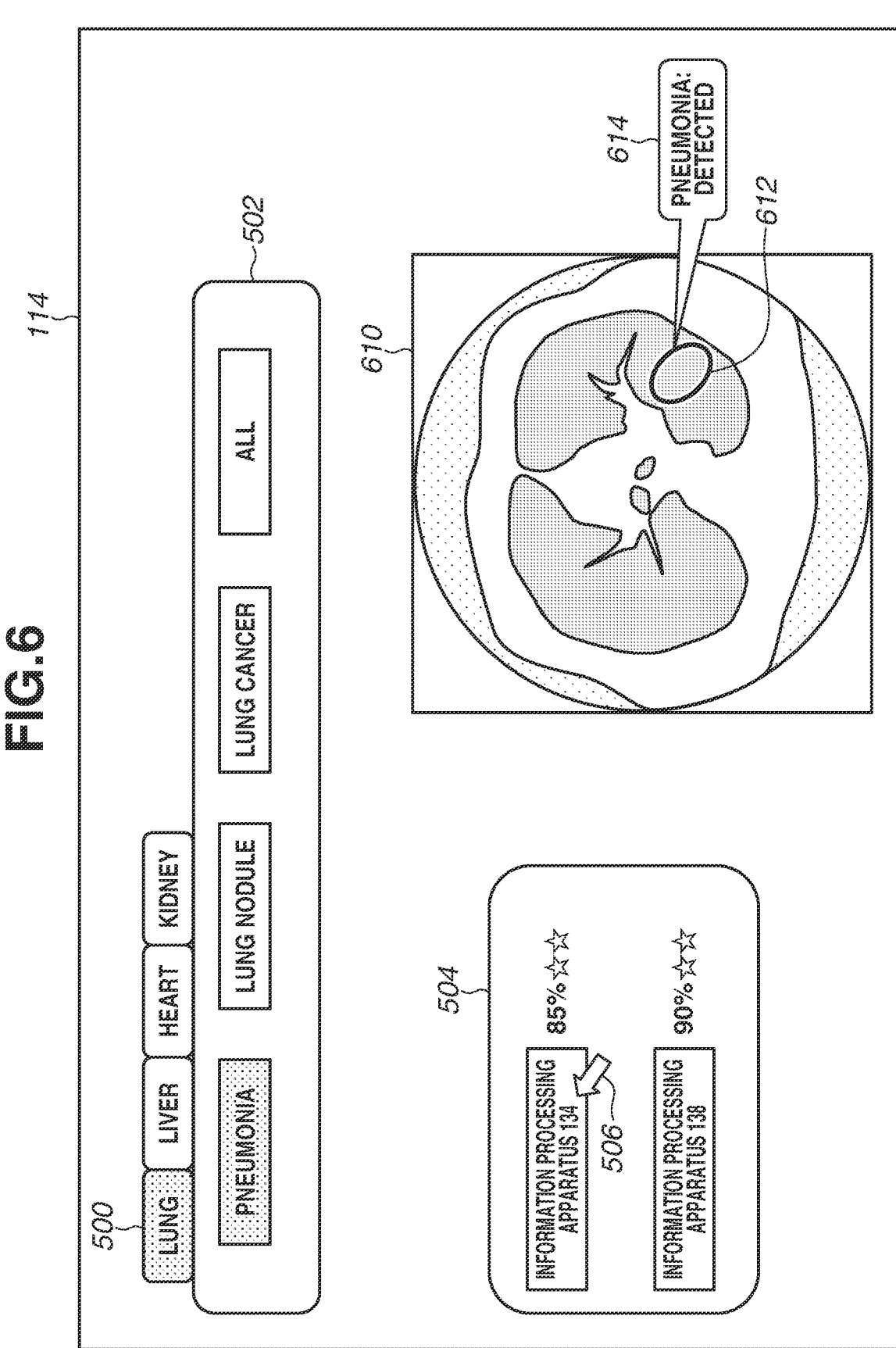
FIG. 6 illustrates one display form of the display unit according to an exemplary embodiment of the present invention.

FIG. 6 illustrates an example of the screen display form of the display unit 114 according to the present exemplary embodiment. FIG. 6 is different from FIG. 5 in that pneumonia is selected on the selection screen 502.

The information terminal 110 can extract the information processing apparatus corresponding to pneumonia by referring to the incidental information (the diagnostic purpose) of the plurality of information processing apparatuses (storage units). On the selection screen 504, the information processing apparatus that can infer pneumonia is displayed. In FIG. 6, the information processing apparatuses 134 and 138 are displayed. The display unit 114 can display the plurality of information processing apparatuses 134 and 138 corresponding to the diagnostic purpose of pneumonia. The operator selects at least one information processing apparatus from the plurality of information processing apparatuses 134 and 138. The operator can select the information processing apparatus using the cursor 506.

In a case where the information processing apparatus 134 is selected by the selection unit 406 of the information terminal 110, the information terminal 110 transmits the medical image data to the information processing apparatus 134 selected by the selection unit 406. The information processing apparatus 134 makes an inference about the transmitted medical image data and transmits an inference result to the information terminal 110. At that time, the information processing apparatus 134 makes an inference about the medical image data transmitted from the information terminal 110 using the trained model that is trained to extract pneumonia in the medical image data. In a case where the medical image data transmitted from the information terminal 110 includes a lesion of pneumonia, the information processing apparatus 134 transmits a diagnostic name and area information about the pneumonia to the information terminal 110.

The display unit 114 displays a medical image 610 based on the medical image data. The medical image 610 is one of a plurality of slice images of a CT image (three-dimensional volume data). The information processing apparatus 134 makes the inference about the medical image data transmitted from the information terminal 110 using the trained model corresponding to pneumonia. As illustrated in FIG. 6, for example, in a case where the inference unit 206 of the information processing apparatus 134 detects a pneumonia in the CT image, the information processing apparatus 134 transmits a diagnostic name and an area information about the pneumonia to the information terminal 110. The display unit 114 displays detection information 614 indicating that a pneumonia is detected. The display unit 114 also displays an area 612 in which the pneumonia is detected.

On the selection screen 504 illustrated in FIG. 6, an information processing apparatus that can infer the pneumonia is displayed. In FIG. 6, the information processing apparatuses 134 and 138 and information about features of the information processing apparatuses 134 and 138 are displayed. The selection unit 406 of the information terminal 110 may select the information processing apparatus based on the incidental information (e.g., the recognition rate) of the plurality of information processing apparatuses 134 and 138.

FIG. 7 illustrates features of the plurality of information processing apparatuses 130 to 138. The features of the plurality of information processing apparatuses 130 to 138 include a region, a diagnostic purpose, a medical image capturing apparatus, a type of learning data, a recognition rate, a number of inference (actual performance) cases, and operator satisfaction. The number of inference cases and the recognition rate are statistical information regarding an inference of each information processing apparatus.

The diagnosis region of the information processing apparatus 130 is a liver and a heart, and the diagnostic purpose is lesion information for a diagnosis of hepatitis, angina, myocardial infarction, and the like. The information processing apparatus 130 can process medical image data of medical image capturing apparatuses of a CT and an MRI. The type of learning data is A. The recognition rate of lesions of hepatitis, angina, and myocardial infarction is 82%. The number of inference cases is 5000 cases. The satisfaction is two stars.

As described above, the information terminal 110 stores the incidental information corresponding to the features of the plurality of information processing apparatuses 130 to 138 connected to the network 120. The plurality of information processing apparatuses 130 to 138 is the information processing apparatus that can be used for an inference about the medical image data from the information terminal 110. The information terminal 110 acquires, from the plurality of information processing apparatuses, incidental information corresponding to the diagnostic purposes that can be inferred by the respective information processing apparatuses in advance.

The display unit 114 displays the incidental information corresponding to the plurality of information processing apparatuses 130 to 138, and thereby the operator can select at least one information processing apparatus from the plurality of information processing apparatuses 130 to 138.

Since the information terminal 110 stores the incidental information corresponding to the diagnosis region and the diagnostic purpose for the plurality of information processing apparatuses 130 to 138, the operator can select the information processing apparatus according to the diagnosis region and the diagnostic purpose as illustrated in FIGS. 5 and 6.

Since the information terminal 110 stores the incidental information corresponding to the medical image capturing apparatus for the plurality of information processing apparatuses 130 to 138, the operator can select an information processing apparatus from the plurality of information processing apparatuses 130 to 138 based on the medical image capturing apparatus.

For example, since the information terminal 110 stores the incidental information corresponding to the recognition rate for the plurality of information processing apparatuses 130 to 138, the operator can select an information processing apparatus having a high recognition rate from the plurality of information processing apparatuses 130 to 138.

Further, since the information terminal 110 stores the incidental information corresponding to the number of inference (actual performance) cases for the plurality of information processing apparatuses 130 to 138, the operator can select an information processing apparatus having a large number of inference (actual performance) cases from the plurality of information processing apparatuses 130 to 138.

Furthermore, since the information terminal 110 stores the incidental information corresponding to the operator satisfaction for the plurality of information processing apparatuses 130 to 138, the operator can select an information processing apparatus having a high operator satisfaction from the plurality of information processing apparatuses 130 to 138.

Figure 8:
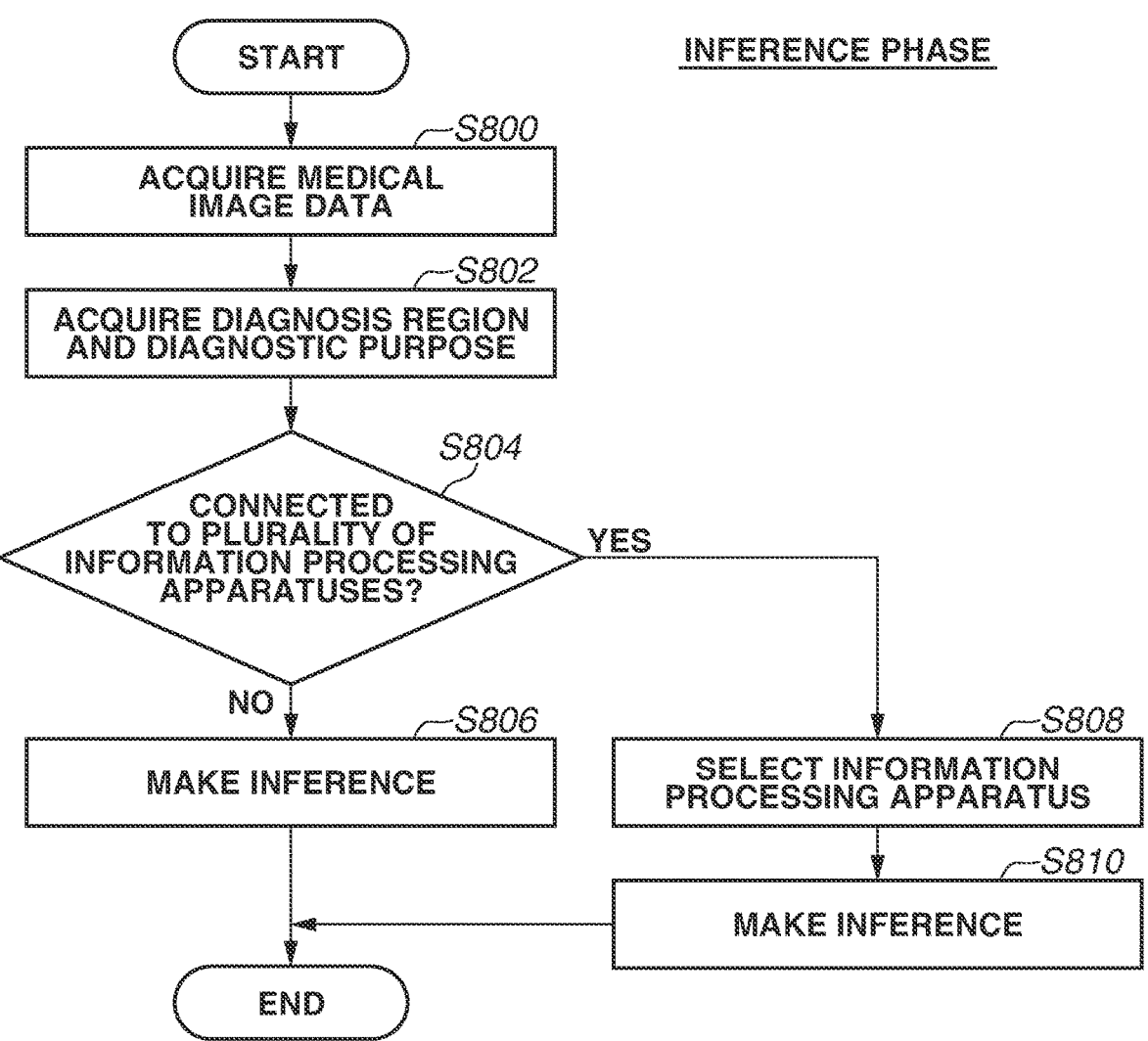
FIG. 8 illustrates operations in an inference phase according to an exemplary embodiment of the present invention.

Operations in an inference phase according to the present exemplary embodiment will now be described with reference to FIG. 8.

In step S800, the medical image capturing apparatus 100 captures an image of an examinee and acquires medical image data.

The information terminal 110 (the image acquisition unit 400) acquires the medical image data from the medical image capturing apparatus 100.

In step S802, the information terminal 110 acquires a diagnosis region and a diagnostic purpose. The operator selects a diagnosis region from a lung, a liver, a heart, a kidney, and the like via the operation unit 112. The diagnostic purpose is a disease name corresponding to the diagnosis region and is the diagnostic purpose (the disease name) that can be inferred by the plurality of information processing apparatuses 130, 132, 134, and others. The operator selects the diagnostic purpose from a lung cancer, pneumonia, and the like via the operation unit 112. The information terminal 110 acquires the diagnosis region and the diagnostic purpose from selection information input from the operation unit 112.

In step S804, the information terminal 110 determines whether it is connected to the plurality of information processing apparatuses via the network 120. In a case where the information terminal 110 is not connected to the plurality of information processing apparatuses (NO in step S804, a case of being connected to one information processing apparatus), the processing proceeds to step S806. In a case where the information terminal 110 is connected to the plurality of information processing apparatuses (YES in step S804), the processing proceeds to step S808.

In step S806, the information terminal 110 transmits the medical image data to the one information processing apparatus connected to the network 120. The information processing apparatus makes an inference about the medical image data using the trained model. The information processing apparatus transmits the inference result obtained by making the inference about the medical image data to the information terminal 110. The display unit 114 displays the inference result obtained by making the inference about the medical image data together with the medical image data.

In step S808, the information terminal 110 selects at least one information processing apparatus from the plurality of information processing apparatuses connected to the network 120. The operator may manually select the information processing apparatus via the operation unit 112, or the information terminal 110 may automatically select the information processing apparatus based on the information (the parameter) based on the incidental information of the information processing apparatus and the statistical information based on the inference.

In step S810, the information terminal 110 transmits the medical image data to the information processing apparatus that is connected to the network 120 and is selected. The selected information processing apparatus makes an inference about the medical image data using the trained model. The selected information processing apparatus transmits an inference result obtained by making the inference about the medical image data to the information terminal 110. The display unit 114 displays the inference result obtained by making the inference about the medical image data together with the medical image data.

As described above, the information processing system according to the present exemplary embodiment includes the information terminal 110 that acquires medical image data from the medical image capturing apparatus 100, the plurality of information processing apparatuses 130, 132, 134, and others each including the inference unit that makes an inference about the medical image data using a trained model, and the selection unit 406 that selects at least one information processing apparatus from the plurality of information processing apparatuses 130, 132, 134, and others. The information terminal 110 transmits the medical image data to the information processing apparatus selected by the selection unit 406, and the information processing apparatus selected by the selection unit 406 makes an inference about the transmitted medical image data and transmits an inference result to the information terminal 110. The information processing system according to the present exemplary embodiment may be provided with the cloud having the plurality of information processing functions each including the inference unit that makes an inference about the medical image data. Further, the information processing system has the plurality of information processing functions 130, 132, 134, and others each including the inference unit that makes an inference about the medical image data using the trained model and the selection unit 406 that selects at least one information processing function from the plurality of information processing functions 130, 132, 134, and others. The information terminal 110 transmits the medical image data to the cloud that executes the information processing function selected by the selection unit 406. The cloud that executes the information processing function selected by the selection unit 406 makes an inference about the transmitted medical image data and transmits an inference result to the information terminal 110.

Further, the information terminal 110 according to the present exemplary embodiment includes the selection unit 406 and the transmission and reception unit 404. The selection unit 406 selects at least one information processing apparatus from the plurality of information processing apparatuses 130, 132, 134, and others each including the inference unit that makes an inference about the medical image data. The transmission and reception unit 404 transmits the medical image data to the information processing apparatus selected by the selection unit 406, and receives an inference result obtained by the information processing apparatus making an inference about the medical image data.

As described above, at least one information processing apparatus can be selected from a plurality of information processing apparatuses and make an inference.

A second exemplary embodiment will now be described. The second exemplary embodiment is different from the first exemplary embodiment in that the selection unit 406 selects at least one information processing apparatus from a plurality of information processing apparatuses based on past inference information (an inference history) of inferences made by the plurality of information processing apparatuses.

Specifically, the information terminal 110 stores the past inference information (the inference history) of the inferences made by the plurality of information processing apparatuses. The selection unit 406 acquires actual performance information of the inferences made by the plurality of information processing apparatuses from the past inference information (the inference history) of the inferences made by the plurality of information processing apparatuses and selects at least one information processing apparatus.

For example, the selection unit 406 selects at least one information processing apparatus from the plurality of information processing apparatuses based on the number of past inference cases inferred by the plurality of information processing apparatuses.

Specifically, the selection unit 406 compares the number of past inference cases inferred by the plurality of information processing apparatuses with each other and selects the information processing apparatus having the largest number of inference cases.

The selection unit 406 can also compare the number of past inference cases inferred by the plurality of information processing apparatuses with each other and select the information processing apparatus in descending order of the number of inference cases. The selection unit 406 may select three information processing apparatuses in descending order of the number of inference cases. The information terminal 110 transmits medical image data to the plurality of information processing apparatuses selected by the selection unit 406. The plurality of information processing apparatuses makes an inference about the medical image data using a trained model. Each of the plurality of information processing apparatuses transmits an inference result obtained by making the inference about the medical image data to the information terminal 110. The information terminal 110 integrates the inference results transmitted from the plurality of information processing apparatuses. The display unit 114 displays the integrated inference result together with the medical image data.

The selection unit 406 can select at least one information processing apparatus from the plurality of information processing apparatuses based on a type of the medical image data acquired from the medical image capturing apparatus 100 and the past inference information of the inferences made by the plurality of information processing apparatuses. Specifically, in a case where the type of the medical image data is CT image data, if the CT image data is included in a target image inferred by the plurality of information processing apparatuses, the selection unit 406 selects the information processing apparatus that includes the CT image data in the inferred target image.

In a case where the type of the medical image data acquired from the medical image capturing apparatus 100 matches the type of the medical image data inferred by at least one information processing apparatus among the plurality of information processing apparatuses, the selection unit 406 selects the at least one information processing apparatus in which the type of the medical image data is matched.

As described above, the selection unit 406 can select at least one information processing apparatus from the plurality of information processing apparatuses based on the past inference information (the inference history) of the inferences made by the plurality of information processing apparatuses. Thus, an operator can select the information processing apparatus used in the past inference information (the inference history) and make an inference.

A computer program for realizing the functions of the above-described exemplary embodiments can be supplied to a computer via a network or a non-transitory computer-readable medium (not illustrated), and the computer program can be executed. The computer program is for causing a computer to execute the above-described information processing method. In other words, the computer program is a program for realizing the function of the information processing apparatus with a computer. The non-transitory computer-readable medium stores the computer program.

According to the present invention, at least one information processing apparatus can be selected from a plurality of information processing apparatuses and make an inference.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-124635, filed Jul. 29, 2021, which is hereby incorporated by reference herein in its entirety.

What is claimed is:

1. An information processing system comprising:
an information terminal including at least one processor and configured to acquire medical image data from a medical image capturing apparatus; and
a plurality of information processing apparatuses each including at least one memory configured to store incidental information on what the information processing apparatus can infer and at least one processor configured to make an inference about the medical image data;

wherein the at least one processor of the information terminal is configured to select at least one information processing apparatus from the plurality of information processing apparatuses,
wherein the at least one processor of the information terminal is configured to present at least one of the plurality of information processing apparatuses as a candidate to a user based on the incidental information acquired from each of the plurality of the information processing apparatuses and a first operation by the user,
wherein the at least one processor of the information terminal is configured to select one of the plurality of the information processing apparatuses to infer from the medical image data based on a second operation of the user to select the one of the plurality of the information processing apparatus from among the candidate,
wherein the information terminal transmits the medical image data to the selected information processing apparatus, and the selected information processing apparatus makes an inference about the transmitted medical image data and transmits an inference result to the information terminal.

2. The information processing system according to claim 1, wherein the information terminal is connected to the plurality of information processing apparatuses via a network.

3. The information processing system according to claim 1, wherein the information terminal is configured to transmit the medical image data to the selected information processing apparatus and to receive an inference result obtained by the selected information processing apparatus making an inference about the medical image data.

4. The information processing system according to claim 1, wherein the incidental information includes to a region that can be inferred by the corresponding information processing apparatus.

5. The information processing system according to claim 4, further comprising a display configured to display the plurality of information processing apparatuses corresponding to a region that can be inferred based on the incidental information.

6. The information processing system according to claim 1, wherein the incidental information includes a diagnostic purpose that can be inferred by each information processing apparatus from the plurality of information processing apparatuses.

7. The information processing system according to claim 6, further comprising a display configured to display a plurality of information processing apparatuses corresponding to a diagnostic purpose that can be inferred based on the incidental information.

8. The information processing system according to claim 1, wherein, in a case where the at least one processor of the information terminal selects the plurality of information processing apparatuses,
the information terminal transmits the medical image data to the plurality of information processing apparatuses selected,
each of the plurality of information processing apparatuses selected makes an inference about the transmitted medical image data and transmits a plurality of inference results to the information terminal, and
the information terminal integrates the plurality of inference results.

9. A method for processing information by using an information processing system comprising a plurality of information processing apparatuses each configured to make an inference about medical image data and an information terminal, the method comprising:

acquiring medical image data from a medical image capturing apparatus;

acquiring incidental information on what each of the plurality of information processing apparatuses can infer;

presenting at least one of the plurality of information processing apparatuses as a candidate to a user based on the incidental information acquired from each of the plurality of the information processing apparatuses and a first operation by the user;

selecting one of the plurality of the information processing apparatuses to infer from the medical image data based on a second operation of the user to select the one of the plurality of the information processing apparatuses from among the candidate;

causing an information terminal to transmit the medical image data to the selected information processing apparatus, and causing the selected information processing apparatus to make an inference about the transmitted medical image data and to transmit an inference result to the information terminal.

10. A non-transitory computer-readable medium storing a program for causing a computer to execute the method according to claim 9.

11. An information terminal to acquire medical image data from a medical image capturing apparatus, the information terminal comprising:

at least one processor configured to execute instructions to perform:

acquiring, from each of a plurality of information processing apparatuses each configured to make an inference about the medical image data, incidental information on what the information processing apparatus can infer;

presenting at least one of the plurality of information processing apparatuses as a candidate to a user based on the incidental information acquired from each of the plurality of the information processing apparatuses and a first operation by the user;

selecting one of the plurality of the information processing apparatuses to infer from the medical image data based on a second operation of the user to select the one of the plurality of the information processing apparatuses from among the candidate;

transmitting the medical image data to the selected information processing apparatus; and receiving an inference result obtained by the selected information processing apparatus making an inference about the medical image data.

* * * * *